(12) United States Patent
Baldwin

(10) Patent No.: US 7,704,519 B1
(45) Date of Patent: Apr. 27, 2010

(54) COMPOSITION AND METHOD FOR DETERRING ANIMALS FROM DAMAGING EXTERIOR SURFACES

(76) Inventor: John Baldwin, 908 Tulane, Houston, TX (US) 77008

( * ) Notice: Subject to any disclaimer, the term of this patent is extended or adjusted under 35 U.S.C. 154(b) by 515 days.

(21) Appl. No.: 11/554,326

(22) Filed: Oct. 30, 2006

(51) Int. Cl.
*A01N 25/00* (2006.01)
*A01N 25/24* (2006.01)
*A01N 37/44* (2006.01)
*A01N 37/10* (2006.01)
*C09D 195/00* (2006.01)

(52) U.S. Cl. .................. 424/405; 424/407; 106/502; 514/485; 514/568; 514/715; 514/722; 514/762; 514/918; 514/920

(58) Field of Classification Search .................. 424/409, 424/405, 407; 106/502; 428/907; 514/485, 514/715, 918, 920, 568, 722; 516/38
See application file for complete search history.

(56) References Cited

U.S. PATENT DOCUMENTS

| 4,661,504 A | 4/1987 | Hollander et al. |
| 4,818,535 A | 4/1989 | Baines et al. |
| 5,352,454 A | 10/1994 | Dyer, Sr. |
| 5,741,553 A | 4/1998 | Manolas et al. |
| 6,908,643 B2 | 6/2005 | Landers |

FOREIGN PATENT DOCUMENTS

WO    WO 9404027 A1 * 3/1994

OTHER PUBLICATIONS

Ingredients-Dimethyl ether [retrieved on Dec. 18, 2008]. Retrieved from the Internet: <URL:http://web.archive.org/web/20040405012223/http://sci-toys.com/ingredients/dimethyl_ether.html.*

J. Russell Mason, Overview of Controls: Why They Work and How They Function, 1997, Wildlife Damage Management for Natural Resource Managers, Western Forestry and Conservation Association, Portland OR, pp. 11-16.*

* cited by examiner

*Primary Examiner*—John Pak
*Assistant Examiner*—Andriae M Holt
(74) *Attorney, Agent, or Firm*—Egbert Law Offices PLLC

(57) ABSTRACT

A composition for application to exterior surfaces, such as trees, so as to prevent animal damage to the exterior surface, has asphalt and denatonium benzoate mixed together. The denatonium benzoate is 1% to 50% by weight of the total composition. The asphalt is between 50% and 60% of the total composition. Naphtha and dimethyl ether are further components of the total composition. The composition is sprayable onto the exterior surface.

3 Claims, No Drawings

COMPOSITION AND METHOD FOR DETERRING ANIMALS FROM DAMAGING EXTERIOR SURFACES

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to methods and compositions for repelling animals. More particularly, the present invention relates to methods and compositions for deterring animals from damaging trees and other wooden exterior surfaces. Additionally, the present invention relates to mixtures of asphalt and denatonium benzoate.

2. Description of Related Art Including Information Disclosed Under 37 CFR 1.97 and 37 CFR 1.98

Ranches, farms and estates often have a large number of trees locate throughout the estate. These trees can be very valuable items on the land. The trees provide shade, provide for water control and prevent erosion. In addition, these trees have extreme aesthetic value to the owner of the land. As such, it is very important to prevent damage to such trees by animals.

In other circumstances, wood is often used in the construction of fences, stalls, corrals and other structures to contain and house animals. These wooden structures are often treated with toxic wood-preserving chemicals. These toxic chemical preservatives can include, but are not limited to, creosote, pentachlorophenol, and arsenic salts, such as copper chromated arsenic. The chewing on and injection of both treated and untreated wood is known to cause several medical problems and even the death of these animals. In addition, the wood chewing can compromise the structural integrity and aesthetic appeal of the wooden structures.

There are prior art sprays that are used for the discouraging of animals from chewing on such trees and wood structures. A product, known as "BITREX"™, is a bittering agent that has been used, in the past, as a pet repellent. In certain circumstances, this bittering agent has been sprayed onto such wooden structures and on the trees. Unfortunately, when sprayed, this product does not remain on the wooden structures for a very long time. Rain and exposure to the outdoor elements, can cause a deterioration of the "BITREX"™ such that the bittering agent is no longer effective. "BITREX"™ is otherwise known as denatonium benzoate.

Since the trees and wooden structures are often distributed throughout the ranch, farm or estate, it is very difficult for the owner, or person responsible for the maintenance of such land, to continually spray this bittering agent onto the wooden structures. Often, fatal damage to the trees could occur before the owner of the land is aware that the bittering agent has degraded.

In other circumstance, treated polyurethanes are used so as to prevent damage to these wooden structures. These water-treated polyurethanes are often sprayed or painted onto the trees. Unfortunately, these urethanes can damage the tree and are often toxic to the health of the tree.

Typically, the animals that are on such ranches, farms and estates have very sensitive mouths and nasal membranes. Horses, in particular, have a habit of "cribbing", i.e. the chewing on wooden objects. Under certain circumstances, the horses will be injured by such chewing activities. In other circumstances, the "cribbing" activities can be rather addictive to the horse such that, under extreme circumstances, the horse prefers to chew on the wood than actually eat food. Horse are known to cause extreme damage to stalls, fences, gates and other wooden structures by this chewing activity. As such, it is very important to prevent the horses from these cribbing activities.

In the past, when bittering agents have been applied to the exterior surfaces, they quickly disperse into the environment and are ineffective. Since the spraying of these bittering agents leaves no visible evidence of application, horses and other animals will forget that they were ever repelled by the bittering agent. As such, although the bittering agent may have been effective for a short period of time, there will be no visible evidence to the animal that the bittering agent had ever been applied to the tree. As such, it is important to provide visible evidence to the animal of the prior existence of the bittering agent. Additionally, it is important to provide visible evidence wherein the land owner is able to determine which wooden structures have been properly treated.

In the past, various patents have issued relating to such composition. For example, U.S. Pat. No. 6,908,643, issued on Jun. 21, 2005 to P. G. Landers, describes a method and composition for deterring animals from chewing on wood. The composition includes iophorone, organo-clay absorber, bisphenol-a-diglycidal ether polymer and a polyamide resin hardener. This composition also has glass flakes and mica therein as well as a microencapsulated acrylic resin-based sealant and a flocculated silica thickener.

U.S. Pat. No. 5,352,454 teaches an anti-chewing and anti-cribbing composition. The exterior surface includes a solvent, a carrier, a non volatile chemical and a pigment. The solvent is a combination of a higher aromatic solvent having a boiling point above 170° C. and crystals thereof combined with a carrier thereof. In particular, this composition is intended for use in association with the cribbing habits of horses.

U.S. Pat. Nos. 4,661,504 and 5,741,553 describe the use of denatonium for preventing pet damage. U.S. Pat. No. 5,741,553 describes the use of a bittering agent of denatonium benzoate (BITREX™). The bittering agent is about 0.03% by weight of the pet repellent. The carrier for this repellent includes tap water, filtered water, softened water and deionized water. This repellent is intended to prevent household pets from damaging furniture, rugs and upholstery. U.S. Pat. No. 4,661,504 issued on Apr. 28, 1987 to Hollander et al., describes the use of denatonium saccharide for the purpose of protecting the surface of an object against animal damage. Surface active agents and hydrocarbons can also be included in the mixture. The composition is intended to be added to paints, pastes, glues and the like.

U.S. Pat. No. 4,818,535 issued on Apr. 4, 1989 to Baines et al., describes a composition for repelling deer. This composition is a synthetic blend of components that is obtained by a Soxhlet extraction of lion faeces.

It is an object of the present invention to provide a composition and method that serves to deter animals from damaging exterior surfaces.

It is another object of the present invention to provide a composition and method that can be retained and be effective when deployed onto the exterior surfaces for a long period of time even through exposure to the exterior environments.

It is another object of the present invention to provide a method and composition for an animal repellent that will not wash off the exterior surface.

It is still another object of the present invention to provide a method and composition for repelling animals that avoids damage to tree and the other exterior surfaces.

It is still a further object of the present invention to provide a method and composition which is easily and clearly visible.

It is still another object of the present invention to provide a method and composition of an animal repellent which is nontoxic to the animal.

It is still another object of the present invention to provide a composition and method which is easy to use, relatively inexpensive and easy to manufacture.

These and other objects and advantages of the present invention will become apparent from a reading of the attached specification and appended claims.

BRIEF SUMMARY OF THE INVENTION

The present invention is a composition for application to trees and other exterior surfaces that comprises asphalt and denatonium benzoate of 1% to 50% by weight of the total composition. In particular, the asphalt is between 50% to 60% by weight of the total composition. Naphtha in an amount of 20% to 30 by weight and dimethyl ether in an amount of 20% to 30% by weight are also added to the total composition. The asphalt and the denatonium benzoate are sprayable. In the preferred embodiment of the present invention, the denatonium benzoate is 10% to 20% of the total composition.

The present invention is also a method of deterring animals from damaging exterior surfaces that comprises the steps of: (1) mixing asphalt and denatonium benzoate together; and (2) spraying the mixture of asphalt and denatonium benzoate onto the exterior surfaces.

In particular, in the method of the present invention the step of mixing includes mixing 1% to 50% by weight of the denatonium benzoate with asphalt. Naphtha and dimethyl ether are also mixed with the denatonium benzoate and asphalt. In the preferred embodiment of the present invention, 20% to 30% by weight of the naphtha and 20% to 30% by weight of the dimethyl ether are mixed with the denatonium benzoate and asphalt. The asphalt should be no less then 50% of the total mixture.

In the method of the present invention, the step of spraying includes pressure spraying the mixture onto the exterior surface in an area accessible by the animal. Alternatively, the mixture can be formed into an aerosol spray. The step of spraying includes aerosol spraying the mixture onto the exterior surface. In the preferred embodiment, this exterior surface is a tree. However, other wooden structures may also be treated by the mixture of the present invention. In particular, the mixture of the present invention is intended to deter the chewing activities of horses. However, the application of the composition of the present invention will deter other animals, such as deer and dogs, from damaging these wooden exterior surfaces.

DETAILED DESCRIPTION OF THE INVENTION

The composition of the present invention includes asphalt mixed with the denatonium benzoate. The denatonium benzoate should be 1% to 50% by weight of the total composition. Preferably, the asphalt is 50% to 60% by weight of the total composition. Additional chemicals, such as naphtha and dimethyl ether, can be added to the composition. Naphtha can be added in an amount of 20% to 30% by weight of the total composition. The dimethyl ether is in an amount of 20% to 30% by weight of the total composition. Preferably, the asphalt and the denatonium benzoate are sprayable.

The composition of the present invention is intended to be sprayed onto exterior surfaces, such as trees. In particular, the asphalt component of the present invention will have a rather dark color. As such, when the mixture of denatonium benzoate and asphalt is applied to a tree, the area of application is easily noticed by the land owner and the animal.

Asphalt is a hydrocarbon which is generally nontoxic to the trees and, in small quantities, nontoxic to any animal consuming the asphalt. As such, when asphalt is applied to plants and trees, the plants and trees will continue to thrive despite the application of asphalt thereto. Since the asphalt is a hydrocarbon-based product, it is immiscible with water. As such, continued exposure to rain, along with the other exterior elements, will not cause the asphalt to break down. The asphalt will retain the denatonium benzoate integrally therewith. Even though the denatonium benzoate would otherwise wash off the surface of the exterior surface, the asphalt serves to retain such bittering agent within the structure of the asphalt itself. There will be a certain amount of surface exposure of the denatonium benzoate from the asphalt. Although the surface-exposed denatonium benzoate could possibly wash off with continued exposure to wind and water, the denatonium benzoate that is retained within the structure of the asphalt will be isolated from the exterior environment. As such, whenever the animal attempts to chew on the wooden structure, the animal will be exposed to that denatonium benzoate that is retained within the structure of the asphalt. As such, the denatonium benzoate will continue to effectively deter the animal for an extremely long period of time. The denatonium benzoate that is retained in the structure of the asphalt will not be exposed to the exterior environment. It is only accessed when the animal chews on the asphalt.

Ultimately, the animal will recognize that it was extremely repelled by such a bittering agent. Even if the denatonium benzoate was ineffective after a prolonged period of time, the animal will continue to recognize the dark coloring on the tree as caused by the asphalt. As such, the animal would visually recognize that the tree had been treated in the past and would be "trained" to avoid such tree. It is believed that application of the composition of the present invention would have a "repelling" effect even if the asphalt contained no denatonium benzoate. The animal would recognize that it was repelled by certain trees having a dark covering and would tend to avoid any other trees that have a similar dark covering.

This composition effectively prevents the "cribbing" activities of horse. Additionally, deer are also repelled by these bittering agents. As a result, the damage caused by horses and deer to exterior wooden structures is effectively deterred.

In the method of the present invention, the asphalt and the denatonium benzoate are mixed together. This mixture can be sprayed onto the exterior surfaces. In particular, the step of mixing includes 1% to 50% by weight of the denatonium benzoate with asphalt. Naphtha and dimethyl ether are also mixed with the denatonium benzoate and asphalt. The asphalt is to be mixed so as to be no less then 50% of the total mixture. The mixture can be pressured sprayed onto the exterior surface in an area accessible by the animal. Alternatively, the mixture can be formed into an aerosol spray and then aerosol sprayed onto the exterior surface in an area accessible by the animal.

The invention composition for deterring animals from damaging exterior surfaces comprises:

asphalt in an amount of at least 50% by weight of the total composition;

denatonium benzoate in an amount of 1% to 10% by weight of the total composition;

naphtha in an amount of at least 20% by weight of the total composition; and dimethyl ether in an amount of at least 20% by weight of the total composition.

Experiments have been conducted with the present invention. Examples of these experiments follow herein:

EXAMPLE I

Experiments have been conducted with the composition having asphalt and denatonium benzoate. In one form of the present invention, the denatonium benzoate is 10% by weight of the total composition. Naphtha is 20% of the total composition, dimethyl ether is 20% of the total composition and asphalt is 50% of the total composition. This produced a black viscous liquid with distinct petroleum order. The boiling point is in excess of 200° F.

Experiments with this composition indicated that it was extremely effective in repelling animals from chewing on trees. Animals were repelled from the tree after an initial taste of the composition. The composition did not damage the tree and was not toxic to the tree. The composition remained on the tree despite continued exposure to the ambient environment.

EXAMPLE II

A composition was tested in which the denatonium benzoate was 1% by weight of the total composition. Asphalt, naphtha and dimethyl ether constitute the remainder of the composition. The asphalt was at least 50% of the total composition. Experiments with this composition showed that such a small amount of denatonium benzoate was not very effective in repelling the animal. The horses continued to chew on the tree despite the presence of such a small amount of denatonium benzoate.

EXAMPLE III

A composition was tested in which the denatonium benzoate constituted 50% of the total composition with asphalt constituting the remainder of the composition. The large amount of denatonium benzoate was very effective in repelling animals. However, this large amount of denatonium benzoate adversely affected the ability of the asphalt to adhere onto the surface of the tree. As such, it was found that compositions that had an excess of 50% denatonium benzoate as mixed with the asphalt would be ineffective in applications to exterior surfaces, such as trees.

EXAMPLE IV

Experiments were conducted in which the denatonium benzoate constituted 20% by weight of the total composition as mixed with asphalt. When applied to trees, this composition was very effective in deterring the animals from damaging the tree.

The foregoing disclosure and description of the invention is illustrative and explanatory thereof. Various changes in the components of the composition or in the steps of the method can be made within the scope of the appended claims without departing from the true spirit of the invention. The present invention should only be limited by the following claims and their legal equivalents.

I claim:

1. A composition for deterring animals from damaging exterior surfaces, the composition comprising:

asphalt in an amount of at least 50% by weight of the total composition;

denatonium benzoate in an amount of 1% to 10% by weight of the total composition;

naphtha in an amount of at least 20% by weight of the total composition; and dimethyl ether in an amount of at least 20% by weight of the total composition.

2. The composition of claim 1, said asphalt and said denatonium benzoate being sprayable.

3. The composition of claim 1, said denatonium benzoate being 10% to 20% of the total composition.

* * * * *